(12) United States Patent
Weinberg et al.

(10) Patent No.: US 12,210,078 B2
(45) Date of Patent: Jan. 28, 2025

(54) APPARATUS AND METHOD FOR C-ARM MRI WITH ELECTROPERMANENT MAGNETS

(71) Applicant: WEINBERG MEDICAL PHYSICS, INC, North Bethesda, MD (US)

(72) Inventors: Irving N. Weinberg, Chevy Chase, MD (US); Oleg Udalov, North Potomac, MD (US)

(73) Assignee: WEINBERG MEDICAL PHYSICS INC., North Bethesda, MD (US)

( * ) Notice: Subject to any disclaimer, the term of this patent is extended or adjusted under 35 U.S.C. 154(b) by 124 days.

(21) Appl. No.: 18/078,661

(22) Filed: Dec. 9, 2022

(65) Prior Publication Data

US 2023/0184855 A1 Jun. 15, 2023

Related U.S. Application Data

(60) Provisional application No. 63/287,808, filed on Dec. 9, 2021.

(51) Int. Cl.
*G01R 33/38* (2006.01)
*A61B 5/055* (2006.01)
*G01R 33/383* (2006.01)

(52) U.S. Cl.
CPC ............ *G01R 33/383* (2013.01); *A61B 5/055* (2013.01)

(58) Field of Classification Search
CPC .......................... G01R 33/383; G01R 33/381; G01R 33/3806; G01R 33/445; A61B 5/055; A61B 5/702; A61B 5/704
See application file for complete search history.

(56) References Cited

U.S. PATENT DOCUMENTS

2008/0306377 A1* 12/2008 Piron ................... A61B 8/5238
324/318
2016/0243377 A1* 8/2016 Weinberg ................. A61N 2/02

FOREIGN PATENT DOCUMENTS

JP H0994234 A * 4/1997
WO WO-2023161775 A1 * 8/2023

OTHER PUBLICATIONS

Machine Translation of JP-H0994234-A1 (Year: 1997).*

* cited by examiner

*Primary Examiner* — G.M. A Hyder
(74) *Attorney, Agent, or Firm* — Barnes & Thornburg LLP

(57) ABSTRACT

A method and apparatus for accessing and imaging at least one body part of interest may position a subject in an imaging system to partially encloses the subject and partially expose the subject, and access at least one body part of the subject that is exposed outside the imaging system for a procedure. The at least one exposed body part is positioned to be imaged by the imaging system.

15 Claims, 4 Drawing Sheets

APPARATUS AND METHOD FOR C-ARM MRI WITH ELECTROPERMANENT MAGNETS

CROSS REFERENCE AND PRIORITY CLAIM

This patent application claims priority to U.S. Provisional Patent Application No. 63/287,808, entitled "APPARATUS AND METHOD FOR C-ARM MRI WITH ELECTROPERMANENT MAGNETS," filed Dec. 9, 2021, the disclosure of which being incorporated herein by reference in its entirety.

FIELD

Disclosed embodiments are directed to diagnosis, therapy or research involving humans or other animals, in particular using a C-arm MRI with electropermanent magnets.

SUMMARY

Disclosed embodiments describe methods and apparatuses for detecting tumors and other lesions or structures of interest in parts of human or non-human animals without obstructing surgical access, using MRI systems that incorporate electropermanent magnets ("EPMs").

In some embodiments, an apparatus may comprise an imaging system that partially encloses a subject and partially exposes the subject. At least one body part of the subject is exposed outside the imaging system to be accessed for a procedure and to be imaged by the imaging system.

In some embodiments, a method of accessing and imaging at least one body part of interest may comprise positioning a subject in an imaging system to partially encloses the subject and partially expose the subject, and accessing at least one body part of the subject that is exposed outside the imaging system for a procedure. The at least one exposed body part is positioned to be imaged by the imaging system.

BRIEF DESCRIPTION OF THE FIGURES

Aspects and features of the disclosed embodiments are described in connection with various figures, in which.

DETAILED DESCRIPTION

Disclosed embodiments will now be described in connection with one or more embodiments. It is intended for the embodiments to be representative of the inventive concept and not limiting of the scope of the inventive concept. The inventive concept is intended to encompass equivalents and variations, as should be appreciated by those skilled in the art.

Surgeons or other medical or veterinary professionals often need to access parts of a body of a human or non-human animal. Conventional MRI systems do not typically provide acceptable access for interventions (for example, biopsy, surgery).

Weinberg US 2017/0227617, "METHOD AND APPARATUS FOR MANIPULATING ELECTROPERMANENT MAGNETS FOR MAGNETIC RESONANCE IMAGING AND IMAGE GUIDED THERAPY," incorporated by reference, teaches how to build an MRI with electropermanent magnets, where electropermanent magnets are defined as components containing a magnetizable material and an electrically conductive material, in which the magnetizable material has remanent magnetization after current flows through the electrically conductive material.

Figure 1:
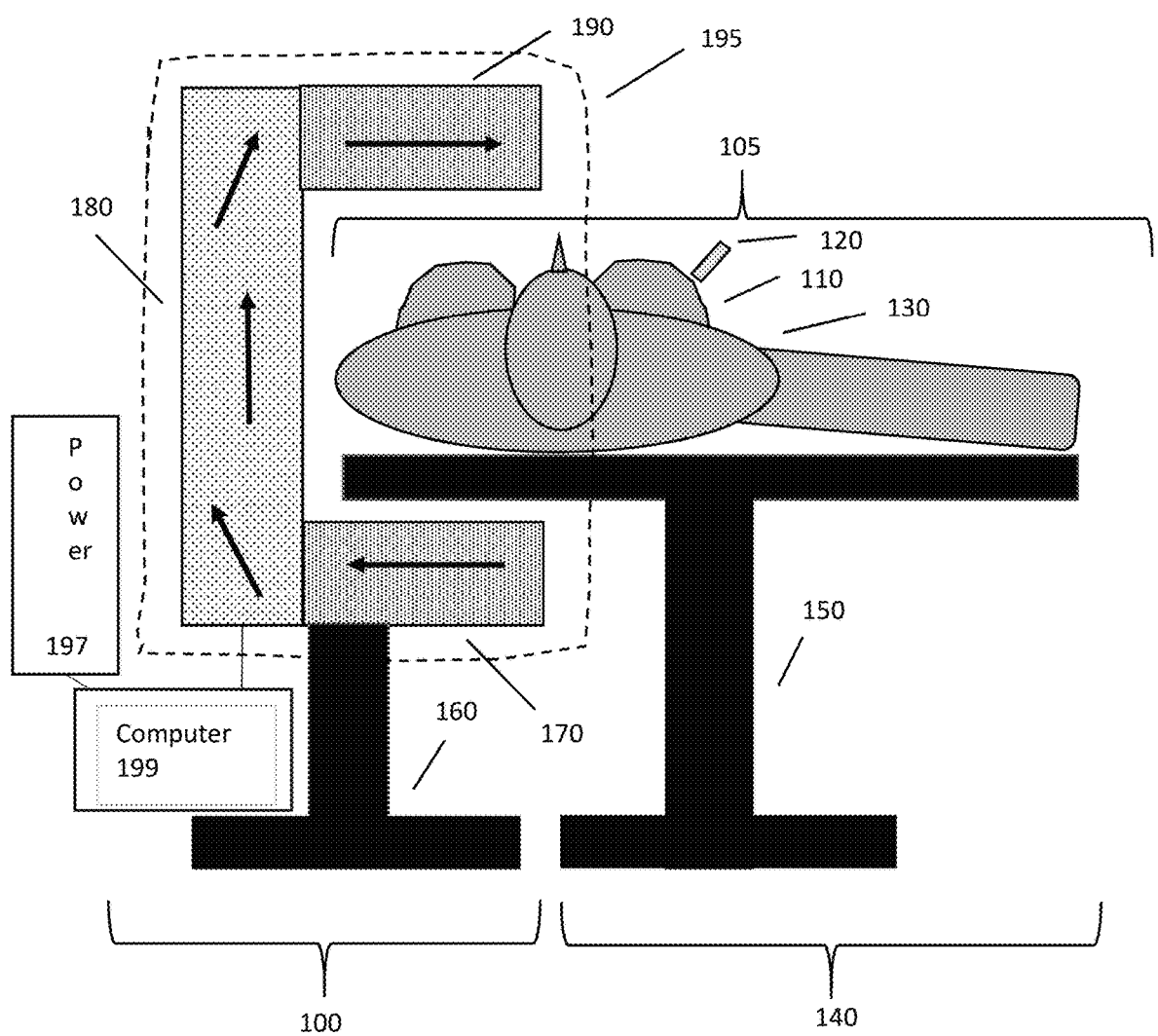
FIG. 1 shows an example of an apparatus enclosing a part of a subject according to the disclosed embodiments.

In FIG. 1, a C-arm or a mobile imaging system 100 may enclose a part of a human or non-human animal subject 105 the subject having a body part 110 within an area of interest, access to which body part 110 is desired to a surgeon or other interventional practitioner. The body part 110 is not enclosed by the imaging system 100 (i.e., it is exposed). The surgeon or other practitioner may access the body part 110 with an instrument 120, for example, a scalpel. The subject is shown extending the arm to uncover an axilla 130, which may be useful if the body part 110 is a breast and the surgeon would like to access the axilla of the subject at some point in the surgical procedure. The imaging system 100 may include a base and support sub-system 160, which may be attached to the floor or may be attached to a ceiling or wall. The subject 105 may rest on a table 140, which may include a base and support sub-system 150. As illustrated, table 140 may be configured so that a portion of table 140 extends outside of and is not enclosed by c-arm of the imaging system 100.

The apparatus of FIG. 1 employs an imaging system 100 including at least three arrays 170, 180, and 190, at least one of which array contains at least one Electro-Permanent Magnets (EPMs) to establish quasi-static magnetic fields and magnetic gradients in the Field-Of-View (FOV) containing the body part 110 to be accessed. The imaging system 100 may include at least one block 170 containing electropermanent magnets, and may also include permanent magnets, whose net magnetization vector is illustrated by an arrow. The term "block" is intended to mean an array or arrays of electropermanent magnets and/or permanent magnets. The imaging system 100 may also include at least one block 180 containing permanent magnets, which may also include electropermanent magnets, whose net magnetization vector is illustrated by several arrows. The imaging system 100 may also include at least one block 190 containing electropermanent magnets, and may also include permanent magnets, whose net magnetization vector is illustrated by an arrow.

The imaging system includes a computer 199, power source 197, and may include one or more radiofrequency antennas not shown. Surface 195 illustrates the minimum surface that includes all parts of the imaging system 100 that generate a magnetic field for imaging (i.e., coils, magnetizable material). Surface 195 does not include the support sub-system 160 or the power supplies or computers required for the imaging system to work. For the purpose of this disclosure, the term "surface" is intended to mean a virtual surface, rather than an actual surface that can be touched. Despite being virtual, the use of surface to describe the geometry of the system and the subject is considered to be a useful construct, since the geometry may affect access to a subject's body part for interventions.

For the purposes of this disclosure, the terms "encloses a part," "enclosing a part," and "enclosed a part" should be understood to mean that a minimum surface 195 covers all surfaces of the imaging system (not including the support section 160 of the imaging system) and includes the part 110. It should also be understood that one or more power supplies or monitors or computers required for operation of the imaging system 100 are also not included within surface 195.

Figure 4:
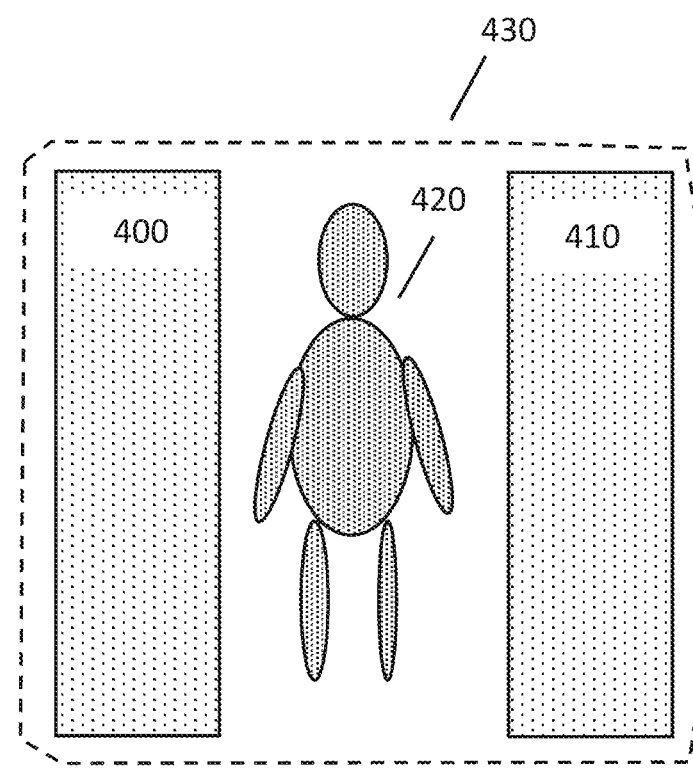
FIG. 4 illustrates a conventional "open MRI", that includes superconducting magnets 400 and 410, which enclose a subject 420 according to the definition for a minimum surface 195 described above for FIG. 1 (i.e., the minimum surface that includes all parts of the imaging system 100 that generate a magnetic field for imaging). Surface 430 demonstrates that the subject is fully enclosed by that definition.

As an illustration of this definition of surface 195, a single-sided MRI placed adjacent to a subject would not be considered to enclose a part of that subject. Under this definition of "enclosed", if the subject's extremity was sticking into a hole within the single-side MRI, then the subject's extremity would be enclosed but the rest of the subject would not be enclosed, i.e. would be exposed. A subject placed within a bore of a conventional toroidal MRI or lying within the three sides of a three-sided conventional MRI ("open MRI") would be completely enclosed. Under this definition of "enclosed", if the subject's extremity was sticking outside the bore of the conventional MRI, then the subject's extremity would not be enclosed. Disclosed embodiments address the case where imaging is collected of a body part 110 that is not enclosed by the imaging system, and where another part of the subject is enclosed by the imaging system. For the purposes of this disclosure, an "open" MRI (as in FIG. 4) completely encloses a subject, since the open MRI is not intended to and cannot successfully image an object that is outside of the minimum surface 430 (as applied to the open MRI). FIG. 4 illustrates a conventional "open MRI", that includes superconducting magnets 400 and 410, which enclose a subject 420 according to the definition for a minimum surface 195 described above for FIG. 1 (i.e., the minimum surface that includes all parts of the imaging system 100 that generate a magnetic field for imaging). Surface 430 demonstrates that the subject is fully enclosed by that definition.

The term quasi-static magnetic field ("B0") should be understood to mean a magnetic field that lasts long enough to polarize protons in the field-of-view (FOV) containing the body part 110 to be accessed.

The apparatus shown in FIG. 1 may create both quasi-static magnetic field for proton magnetizing and imaging magnetic gradients. This creation may be achieved through the use of combination of permanent and electropermanent magnets.

Although FIG. 1 illustrates a subject in the FOV of the imaging system 100, it should be understood that tissues removed from a subject could also be imaged, i.e., by replacing the entire subject with the tissues from the subject, as described in operation 240.

Although FIG. 1 illustrates magnetization orientations (through arrows shown in FIG. 1) that will provide a magnetic field in the region of body part 110 with uniformity in at least one plane that is better than 3 mT, it should be understood that other magnetization orientations may be employed to collect images.

Figure 2:
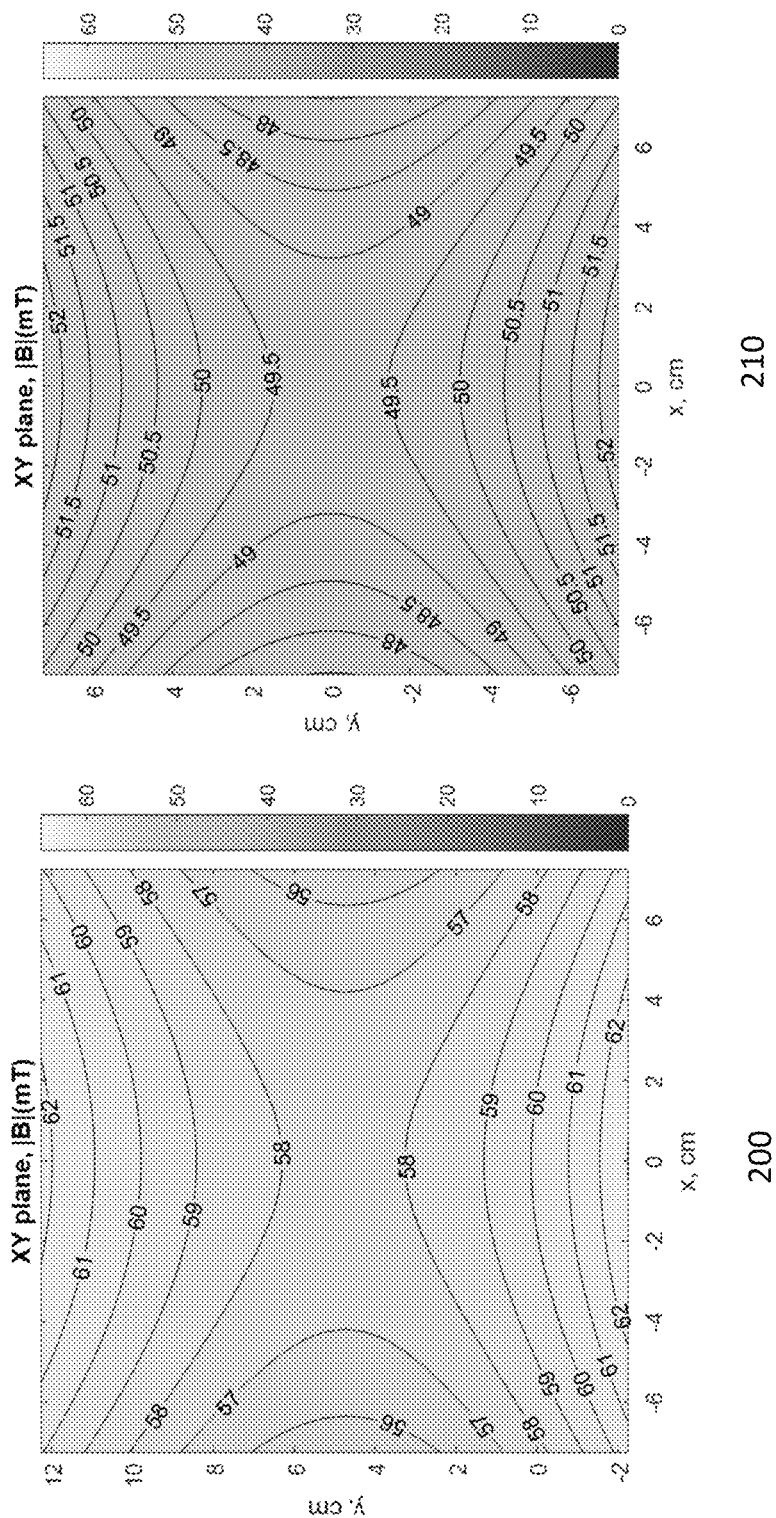
FIG. 2 shows magnetic field profiles collected in sagittal planes at the location of body part and at the axilla, respectively, when the magnetic orientations of apparatus arrays are as shown as in FIG. 1.

FIG. 2 shows that the magnetic field profiles in a sagittal plane at locations 110 and 130 may be made fairly uniform (i.e., within 3 mT). The uniformity may be helpful in conducting magnetic resonance imaging (MRI), as is well-appreciated in the field of MRI. In FIG. 2, the magnetic field profiles 200 and 210 are collected in sagittal planes at the location of body part 110 and at the axilla 130, respectively, when the magnetic orientations of arrays of blocks 170, 180, and 190 are shown as in FIG. 1.

Figure 3:
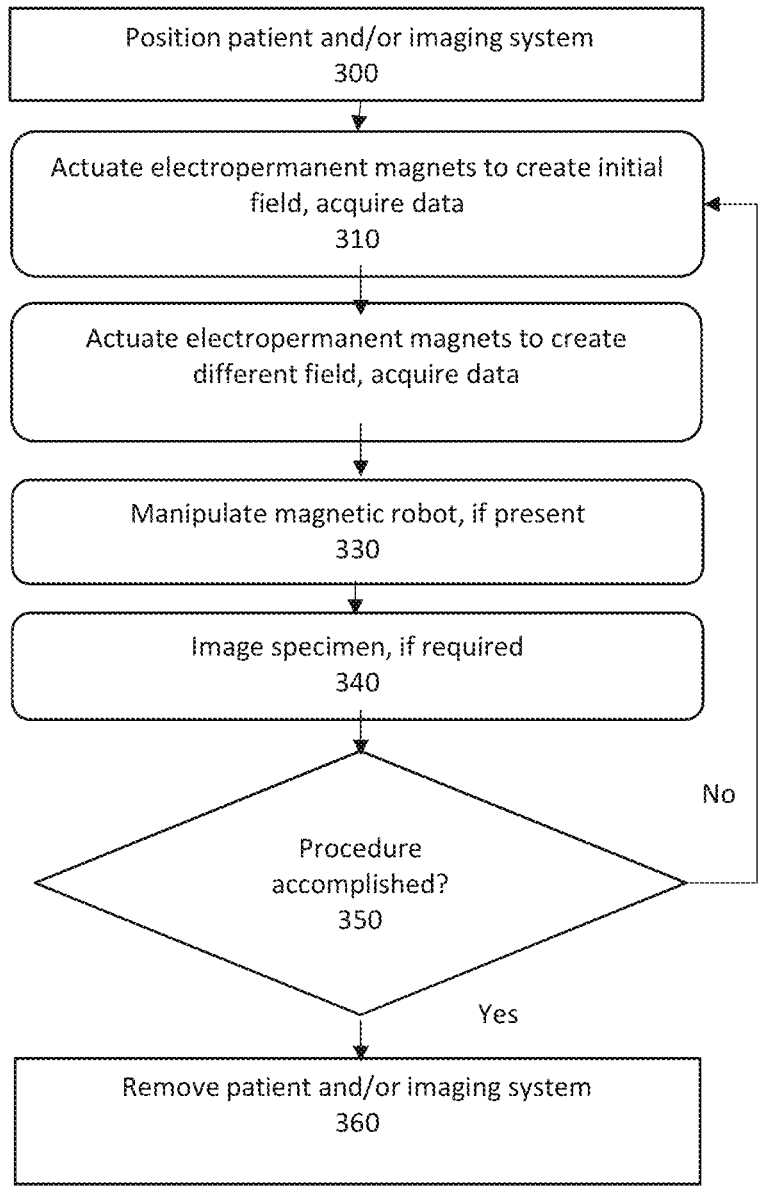
FIG. 3 shows an example of one embodiment of a method according to the disclosed embodiments.

In FIG. 3, a method begins with operation 300: positioning of the subject ("patient") 105 and/or imaging system 100 so that at least one body part 110 of the subject 105 is exposed for access during an anticipated procedure (e.g., surgical excision of a tumor). In other words, the patient is placed partially in the imaging system (operation 300), where the imaging region including body part 110 is outside of enclosed region 195. In operation 310, electropermanent magnets are actuated to create initial magnetic field configuration, and data are collected to assist in forming a magnetic resonance image. In operation 320, electropermanent magnets may be actuated to create another magnetic field configuration, and data are collected to assist in forming a magnetic resonance image.

One of the magnetic field configurations may have a different static field, in which case information could be collected about the tissue characteristics, as described in the provisional application 63/279,524 [placeholder for utility application number], by Irving Weinberg entitled "METHOD FOR INTRINSIC CONTRAST MRI WITH ELECTROPERMANENT MAGNETS", incorporated by reference. Magnets (permanent and/or electropermanent) create quasi-static magnetic field, which can magnetize protons in the body part 110. Several different magnetic configurations can be applied by actuating the electropermanent magnets in different magnetizations and different timings in operations 310 and 320. In operation 330, intervention or other manipulations may be performed without removing a patient from the apparatus in the imaged non-enclosed region.

For example, electropermanent magnets may be actuated to manipulate magnetizable tools ("magnetic robots"). In operation 340, an image of a specimen or tissue removed from the patient may be optionally collected with the imaging system. Tissues removed from the body part may be imaged using the system, potentially with different static fields as described by V. Bitonto et al., "Low-Field NMR Relaxometry for Intraoperative Tumour Margin Assessment in Breast-Conserving Surgery," Cancers, vol. 13, no. 16, p. 4141, August 2021, doi: 10.3390/cancers13164141, incorporated by reference. In operation 350, a decision is made by the operator (or robotic system controlling the imaging system) as to whether the planned procedure has been accomplished. If the procedure has been completed, then in operation 360 the patient and/or imaging system is removed, otherwise some or all of the previous operations are repeated.

Those skilled in the art will recognize, upon consideration of the above teachings, that the above exemplary embodiments and the control system may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Moreover, it should be understood that control and cooperation of the above-described components may be provided using software instructions that may be stored in a tangible, non-transitory storage device such as a non-transitory computer readable storage device storing instructions which, when executed on one or more programmed processors, carry out the above-described method operations and resulting functionality. In this case, the term "non-transitory" is intended to preclude transmitted signals and propagating waves, but not storage devices that are erasable or dependent upon power sources to retain information.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and non-volatile storage technologies without departing from certain embodiments. Such alternative storage devices should be considered equivalents.

While various exemplary embodiments have been described above, it should be understood that they have been presented by way of example only, and not limitation. Thus, the breadth and scope of the present inventive concept should not be limited by any of the above-described exemplary embodiments but should instead be defined only in accordance with the following claims and their equivalents.

The invention claimed is:

1. An apparatus comprising:
an imaging system that partially encloses a subject within a volume having a boundary (195) defined by a minimum surface of all coils or magnetizable material of the imaging system and partially exposes the subject outside of the minimum surface,
wherein at least one body part of the subject is exposed outside the minimum surface while being accessed for a procedure and while being imaged by the imaging system without moving the subject.

2. The apparatus of claim 1, where the imaging system includes at least one electropermanent magnet and at least one permanent magnet.

3. The apparatus of claim 1, where the imaging system is configured to vary a quasi-static magnetic field for the body part.

4. The apparatus of claim 1, wherein the imaging system includes a combination of permanent and electropermanent magnets configured to create both a uniform imaging field and imaging gradients in the exposed part of the subject.

5. The apparatus of claim 1, wherein the imaging system is configured to provide access to and imaging of the at least one exposed body part without moving the subject between the procedure and imaging.

6. The apparatus of claim 1, wherein the imaging system comprises at least three arrays, wherein at least one of the arrays contains at least one electropermanent magnet to establish quasi-static magnetic fields and magnetic gradients in a field-of-view containing the at least one body part to be accessed.

7. The apparatus of claim 1, wherein the imaging system comprises a c-shaped arm formed of three arrays, wherein at least one of the three arrays contains at least one electropermanent magnet.

8. The apparatus of claim 1, further comprising a table configured to support the subject and the at least one body part, wherein the imaging system comprises a c-shaped arm and a portion of the table extends outside the c-shaped arm to expose the at least one body part for access.

9. A method of accessing and imaging at least one body part of interest comprising:
positioning a subject in an imaging system to partially enclose the subject within a volume having a boundary (195) defined by a minimum surface of all coils or magnetizable material of the imaging system and partially expose the subject outside the minimum surface, and
accessing at least one body part of the subject that is exposed outside the minimum surface for a procedure, wherein the at least one body part is exposed outside minimum surface while imaged by the imaging system and wherein the at least one body part is accessed and imaged without moving the subject.

10. The method of claim 9, wherein the imaging system includes at least one electropermanent magnet.

11. The method of claim 9, wherein the imaging system includes a combination of permanent and electropermanent magnets configured to create both a uniform imaging field and imaging gradients in the exposed part of the subject.

12. The method of claim 9, wherein the imaging system is configured to provide access to and imaging of the at least one exposed body part without moving the subject between the procedure and imaging.

13. The method of claim 9, wherein the imaging system comprises at least three arrays, wherein at least one of the arrays contains at least one electropermanent magnet to establish quasi-static magnetic fields and magnetic gradients in a field-of-view containing the at least one body part to be accessed.

14. The method of claim 9, wherein the imaging system comprises a c-shaped arm formed of three arrays, wherein at least one of the arrays contains at least one electropermanent magnet.

15. The method of claim 9, further comprising a table configured to support the subject and the at least one body part, wherein the imaging system comprises a c-shaped arm and a portion of the table extends outside the c-shaped arm to expose the at least one body part for access.

* * * * *